United States Patent [19]

Matsumura et al.

[11] Patent Number: 4,533,750

[45] Date of Patent: Aug. 6, 1985

[54] PROCESS FOR ISOLATING METHACRYLIC ACID BY EXTRACTION

[75] Inventors: Hiroshi Matsumura; Masato Otani; Fumiki Murakami, all of Otake, Japan

[73] Assignee: Mitsubishi Rayon Co. Ltd., Tokyo, Japan

[21] Appl. No.: 169,808

[22] Filed: Jul. 17, 1980

[30] Foreign Application Priority Data

Jul. 19, 1979 [JP] Japan .................................. 54-91991

[51] Int. Cl.$^3$ ...................... C07C 51/48; C07C 57/05; C07C 57/055

[52] U.S. Cl. .................... 562/600; 562/532; 562/535; 562/538; 562/545

[58] Field of Search ............... 562/600, 532, 535, 545, 562/546, 547, 538, 534

[56] References Cited

U.S. PATENT DOCUMENTS

| | | | |
|---|---|---|---|
| 3,478,093 | 11/1969 | Nonnenmacher et al. | 562/600 |
| 3,781,332 | 12/1973 | Sato et al. | 562/600 |
| 3,968,153 | 7/1976 | Ohrui et al. | 562/600 |

FOREIGN PATENT DOCUMENTS

| | | |
|---|---|---|
| 976043 | 3/1951 | France . |
| 53-50286 | 5/1978 | Japan . |
| 1235634 | 6/1971 | United Kingdom . |
| 154259 | 7/1963 | U.S.S.R. . |

OTHER PUBLICATIONS

Frolov et al., Chemical Abstracts, vol. 60, No. 4, 4012f, 1964, Columbus, Ohio:Extraction of Methacrylic Acid from Solutions.

*Primary Examiner*—Vivian Garner
*Attorney, Agent, or Firm*—Oblon, Fisher, Spivak, McClelland & Maier

[57] ABSTRACT

A process for isolating methacrylic acid by solvent extraction from an aqueous methacrylic acid solution obtained from a gas phase catalytic oxidation reaction, characterized in that the aqueous methacrylic acid solution is previously first contacted with an extraction solvent, polymers precipitated out from the aqueous methacrylic acid solution are removed and the remainder is fed into an extraction column.

4 Claims, 2 Drawing Figures

PROCESS FOR ISOLATING METHACRYLIC ACID BY EXTRACTION

BACKGROUND OF THE INVENTION

1. Field of the Invention

The present invention relates to a process for isolating methacrylic acid by extraction. More particularly, the present invention relates to a process for isolating methacrylic acid from an aqueous methacrylic acid solution obtained by the gas phase catalytic oxidation reaction of one or more of isobutylene, tert. butyl alcohol, methacrolein or isobutyladehyde by extraction in an extraction column.

2. Description of the Prior Art

Methacrylic acid obtained from one or more of isobutylene, tert. butyl alcohol, methacrolein or isobutylaldehyde by gas phase catalytic oxidation reaction is purified generally by absorbing the reaction product obtained by the gas phase oxidation reaction in water, distilling the liquid to remove low-boiling products such as acetone and methacrolein, separating methacrylic acid from water in the extraction step and separating methacrylic acid from the extraction solvent by distillation. However, if said extraction process is carried out continuously, polymers deposit in large amounts in the extraction column or at an interfacial surface part in the extraction step to make the operation in the extraction column impossible after a relatively short period of time. As a result, the inside of the column must be washed every 3-7 days which is disadvantageous. Further, the emulsion is apt to be formed in an upper part of the extraction column, which emulsion often causes flooding, resulting in suspension of the operation in the extraction column each time.

The emulsion thus formed is different from an emulsion formed, for example, when the rotation rate of a rotary extraction column is extremely high. The former emulsion comprises foam with bubble diameter of around 1 mm. It is formed even when rotation rate of the extraction column is low and produces a so-called emulsion phase in addition to the solvent phase and aqueous phase in the extraction column. Once the emulsion phase has been produced, the continuation of the operation in the extraction column becomes impossible unless the emulsion phase is taken out from the extraction column.

After intensive investigation to overcome those problems, it has been found that the emulsion formation is caused by high-boiling materials mainly comprising methacrylic acid polymer.

A need, therefore, continues to exist for a process for extracting methacrylic acid from an aqueous methacrylic acid solution which contains high boiling materials mainly comprising methacrylic acid polymer.

SUMMARY OF THE INVENTION

Accordingly, one object of the invention is to provide an efficient and economical process for isolating methacrylic acid.

Another object of the invention is to provide a process for isolating methacrylic acid which minimizes loss of the extracting solvent during its recovery.

Briefly, these objects and other objects of the invention as hereinafter will become readily apparent can be attained by providing a process for isolating methacrylic acid by solvent extraction from an aqueous methacrylic acid solution obtained from the gas phase catalytic oxidation reaction, characterized in that the aqueous methacrylic acid solution is previously first contacted with an extraction solvent, polymers precipitated out from the aqueous methacrylic acid solution are removed and the remainder is fed into the extraction column.

BRIEF DESCRIPTION OF THE DRAWINGS

FIG. 1 shows an independent feed of solvent to the contact.

FIG. 2 shows recycle of solvent from the extraction column to the contact.

DETAILED DESCRIPTION OF THE PREFERRED EMBODIMENTS

Figure 1:
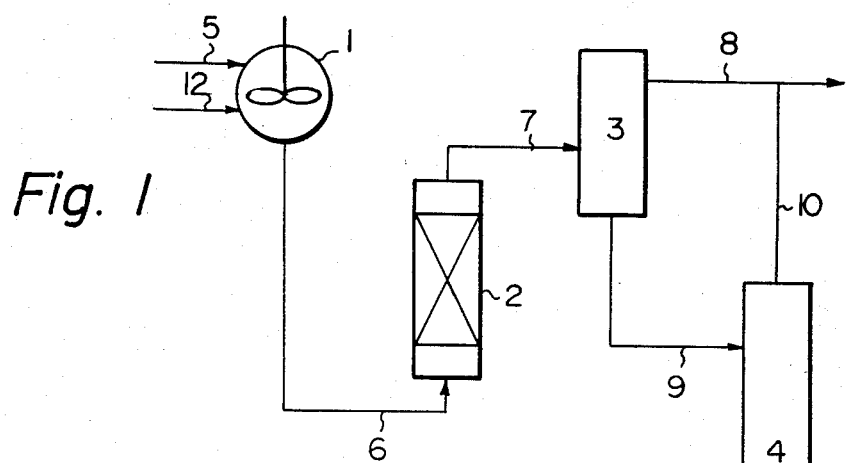
FIGS. 1 and 2 are flow sheets showing preferred embodiments of the present invention.

The present inventors have found that the emulsion does not result and polymers are not deposited if the aqueous methacrylic acid solution is, prior to extraction, contacted with an extraction solvent, and polymers thus precipitated are removed, preferably after such contact the liquid phases in the residue are divided into two phases in a decanter and the aqueous phase is fed in the extraction column. The same solvent can be used for the contact and the extraction. In one embodiment the solvent for the contact is obtained from the extraction column. For example, the solvent phase from the top of the column is passed to the contact. The aqueous methacrylic acid solution can be contacted with the solvent at ambient temperature and, more preferably, at a temperature in the range of 30°-50° C.

For removal of the precipitated polymer, it is preferred to select a suitable filter for removing the polymers precipitated. Though the polymers from a bulky solid together with the extraction solvent and methacrylic acid, the polymers per se are very fine particles and adhesive. Therefore, the polymers clog ordinary glass filters, sintered metal filters and paper filters within a short period of time. If pressure difference on the filter is made too large, the polymers leak out with unfavourable results.

If a rough metal gauze filter or filter cloth is used, the polymers pass through to form an emulsion in a decanter, thereby making it difficult to divide the filtrate into two layers.

if a filter back-washable with water is used, a cake on the surface of the filter cannot be removed completely. In addition, a device is required to treat the back wash solution and this is economically disadvantageous since the filter cake contains the polymers, extraction solvent and methacrylic acid.

After investigation for the purpose of obtaining a filter which is not clogged in a short period of time and which causes only a minimum loss of the extraction solvent, it has been found that packing filters exhibit particularly excellent results in the present invention. Those filters include filters filled with McMahon packing, stainless steel sponges made of extremely fine filaments of stainless steel and metal gauze rings. Those packings have a void space as high as 90-98%. Therefore, the bulky solid comprising the extraction solvent, aqueous methacrylic acid solution and the polymers can be captured directly in the voids. As compared with conventional filters, the packing filters can be used for a far longer period of time without causing leakage of the polymers or formation of emulsion in the decanter.

In the regeneration of the filter, the filter is drained and washed with an aqueous alkali solution, whereby the solid is dissolved easily. Surprisingly, the washed alkali solution contains the extraction solvent only in a quantity soluble in water, though the initial solid comprises the three components, i.e. the extraction solvent, aqueous methacrylic acid solution and polymers. A reason is considered to be that the extraction solvent is eliminated from the bulky solid captured therein as time elapses. Thus loss of the extraction solvent in the regeneration step is negligible. This regeneration process is very economical.

As the extraction solvents suitable for the present invention, there may be mentioned hydrocarbons of 4–8 carbon atoms and/or ketones, ethers and esters of 4–8 carbon atoms effective for the isolation of methacrylic acid by extraction. More concretely, the extraction solvents include n-hexane, n-heptane, benzene, toluene, xylene, ethylbenzene, cyclohexane, methyl isobutyl ketone, isopropyl ether, ethyl acetate, methyl methacrylate and mixtures.

Figure 2:
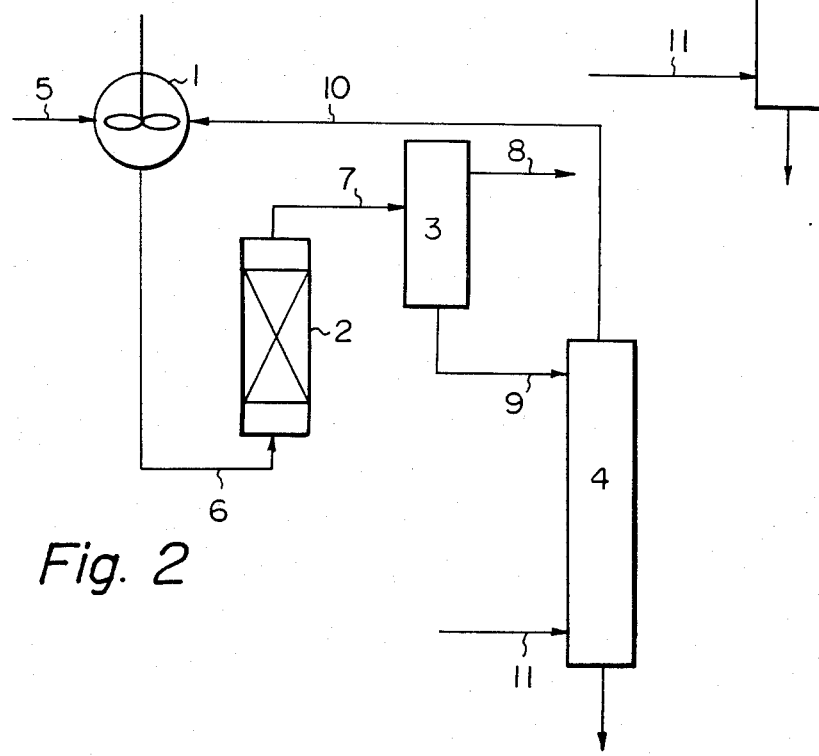

Those extraction solvents in purified form may be fed to a mixing tank to contact with the aqueous methacrylic acid solution as shown in FIG. 1. Alternatively, a part of or the whole solvent phase entering from the top of an extraction column may be used for the contact as shown in FIG. 2. If the whole extraction solvent phase containing methacrylic acid which has exited from the top of the extraction column is fed into the mixing tank in which it is to be mixed with the aqueous methacrylic acid solution, then the extracted methacrylic acid is transferred into an upper layer (organic layer) in the decanter (to be used after the removal of the polymers as described below). The methacrylic acid can be separated and recovered in the subsequent solvent-recovery step. The solvent from which methacrylic acid has been recovered can be circulated again into the extraction column and/or into the mixing tank in which it is to be contacted with the aqueous methacrylic acid solution.

FIGS. 1 and 2 show embodiments of the polymer-removing steps according to the present invention. The process of the present invention will be described with reference to FIGS. 1 and 2.

In the embodiment shown in FIG. 1, an aqueous methacrylic acid solution is fed into a mixing tank 1 through line 5 and an extraction solvent is fed therein through line 12, and they are mixed together in the mixing tank. The liquid mixture is sent through line 6 to a filter 2 where the polymers are removed. Then, the mixture is introduced through line 7 into a decanter 3 and there divided therein into two layers. The organic layer is sent to a solvent recovery step through line 8. The aqueous layer is sent to an extraction column 4 through line 9. The solvent phase discharged from the top of the extraction column is sent to the solvent-recovery step through line 10. An extraction solvent is fed into the extraction column through line 11.

In the embodiment shown in FIG. 2, an aqueous methacrylic acid solution is fed in a mixing tank through line 5 and a solvent phase from the top of the extraction column is fed therein through line 10, and they are mixed together in the mixing tank. A liquid mixture is sent through line 6 to the filter 2 and the polymers are removed. The filtrate is introduced through line 7 into the decanter 3 and divided therein into two layers. The organic layer is sent to a solvent-separating step through line 8 and the aqueous layer is fed into the extraction column 4 through line 9. An extraction solvent is fed into the extraction column through line 11.

The following examples further illustrate the present invention, but are not intended to be limiting the scope of the invention.

EXAMPLE 1

Methacrolein was catalytically oxidized with a phosphorus-molybdenum type oxidation catalyst is gas phase in the presence of air and steam. The resulting oxidation reaction product was recovered by means of water. Low-boiling matters were distilled out to obtain 20 wt.% aqueous methacrylic acid solution. The aqueous methacrylic acid solution was fed in the mixing tank 1 kept at 45° C. at a rate of 5 Kg/hr. as shown in FIG. 2. A solvent phase discharged from the top of an extraction column was added thereto at a rate of 3.8 Kg/hr. to obtain a mixture. Polymers thus precipitated out were filtered out and the filtrate was divided into two layers in the decanter. The aqueous layer was fed into the top of rotary disc extraction column of 46 m/m$\phi$×40 stages. 3.5 Kg/hr. of toluene was fed into the column through the bottom.

After continuous operation for 90 days, polymer deposition in the column was only slight and emulsion formation was not noted at all in the extraction column. The operation could be carried out on a stable basis.

COMPARATIVE EXAMPLE 1

5 Kg/hr. of the same aqueous methacrylic acid solution as in Example 1 was directly fed into a rotary disc extraction column of 46 m/m$\phi$×50 stages through the top thereof. 3.5 Kg/hr. of toluene was fed in the column through the bottom thereof.

Within one day of operation, the polymer deposition began. On the third day, flooding began due to an emulsion formation. On the fifth day, the operation became impossible because fluidity was insufficient due to deposits in the column.

EXAMPLE 2

5 Kg/hr. of the same aqueous methacrylic acid solution as in Example 1 and 1 Kg/hr. of n-heptane were fed in the mixing tank kept at 45° C. shown in FIG. 1 to obtain a mixture. Polymers precipitated out were filtered out and the filtrate was divided into two layers in a decanter. The organic layer was sent to the solvent-recovery step. The aqueous layer was fed into a rotary disc extraction column of 46 m/m$\phi$×40 stages through the top thereof.

2.5 Kg/hr. of n-heptane was fed to the column through the bottom thereof. A solvent phase discharged from the top of the extraction column was sent to the solvent-recovery step.

After the continuous operation for 90 days, polymer deposition in the column was only slight. The operation could be carried out quite on a stable basis.

EXAMPLE 3

Tert. butyl alcohol was oxidized in two steps with a molybdenumbismuth-antimony type catalyst and phosphorus-molybdenum type catalyst in the presence of air and steam. The resulting oxidation reaction product was recovered by means of water. Low-boiling substances were distilled out to obtain 20 wt.% aqueous methacrylic acid solution. 5 Kg/hr. of the aqueous methacrylic acid solution and 2.9 Kg/hr of the solvent phase from the top of the extraction column were fed in the mixing tank kept at 45° C. according to the flow sheet of FIG. 2 to obtain a mixture. Polymers thus precipitated out were filtered out and the filtrate was divided into two layers in a decanter. The organic layer was sent to the solvent-recovery step. The aqueous layer was fed in a rotary disc extraction column of 46 m/mφ×40 stages through the top thereof.

2.5 Kg/hr. of an extraction solvent mixture of toluene and methyl methacrylate (weight ratio: 1:1) was fed into the column through the bottom thereof.

After the continuous operation for 180 days, polymer deposition in the column was slight and emulsion was not formed in the upper part of the extraction column. The operation could be carried out quite on a stable basis.

COMPARATIVE EXAMPLE 2

5 Kg/hr. of the same aqueous methacrylic acid solution as in Example 3 was directly fed into a rotary disc extraction column of 46 m/mφ×50 stages through the top thereof. 2.5 Kg/hr. of an extraction solvent mixture of toluene and methyl methacrylate (weight ratio: 1:1) was fed into the column through the bottom thereof.

The similar results to those obtained in Comparative Example 1 were obtained. On the seventh day, the operation became impossible.

EXAMPLE 4

The same procedure as in Example 3 was repeated except that 74 g of 50μ stainless steel sponge was filled in a depth of 19 cm and 190 g of ⅜ inch McMahon was filled in a depth of 76 cm thereon in a cylinder of 35.2 m/mφ×1000 m/m to prepare a packing type filter. The operation was carried out at 45° C. Exchange time of the filter was 120 hrs. and differential pressure of the filter at the time of the exchange was 530 mmHg. When 50μ ring filter (filtration area: 7 cm$^2$) was used for removing the polymers, exchange time of the filter was 4 hrs. It was thus found that the exchange time was far shorter than that of the packing type filter.

What we claim is:

1. A process for isolating methacrylic acid by solvent extraction from an aqueous methacrylic acid solution obtained from a gas phase catalytic oxidation reaction, which comprises:

contacting and mixing the said aqueous methacrylic acid solution with an extraction solvent precipitating and removing polymeric material from said mixture, decanting said mixture from which polymeric material has been removed, to form an organic phase and an aqueous solution, extracting methacrylic acid from said latter aqueous solution with an extraction solvent in an extraction column, removing a solvent phase from said extraction column, and recovering the methacrylic acid from said solvent.

2. A process according to claim 1 characterized in that the polymers are removed by filtration through a packing filter.

3. The process of claim 1 wherein said decanting separates an organic phase containing methacrylic acid in a solvent from an aqueous phase containing methacrylic acid, and recovering methacrylic acid from said organic phase and wherein said methacrylic acid-solvent solution from said extraction column is supplied to said contacting step.

4. The process of claim 1 wherein said decanting separates an organic phase containing methacrylic acid in a solvent from an aqueous phase containing methacrylic acid; and wherein said organic phase is combined with said methacrylic acid-solvent solution from said extraction column.

* * * * *